United States Patent [19]

Morris

[11] Patent Number: 4,755,413

[45] Date of Patent: Jul. 5, 1988

[54] APERTURED FILM FACING AND METHOD OF MAKING THE SAME

[75] Inventor: Ronald R. Morris, Watchung, N.J.

[73] Assignee: Chicopee, New Brunswick, N.J.

[21] Appl. No.: 866,830

[22] Filed: May 22, 1986

[51] Int. Cl.⁴ .............................................. B32B 3/10
[52] U.S. Cl. .................................... 428/138; 428/137; 428/220; 604/383; 604/378
[58] Field of Search ............... 428/137, 138, 132, 220, 428/131; 604/383, 378

[56] References Cited

U.S. PATENT DOCUMENTS 1,978,620 10/1934 Brewster .............................. 428/119
4,617,326 10/1986 Bjornberg et al. .............. 604/383 X Primary Examiner—Alexander S. Thomas

[57] ABSTRACT

An apertured plastic film facing material and method for making the same, together with an improved absorbent product formed therefrom, wherein the edge of the apertures is coated with a hydrophilic material.

6 Claims, 2 Drawing Sheets

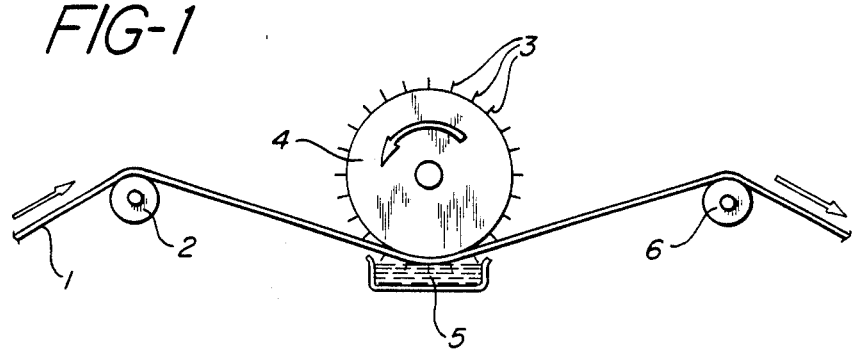
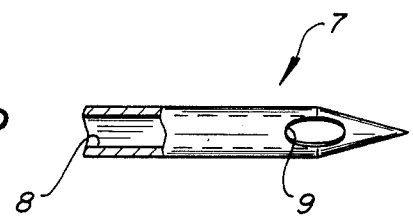
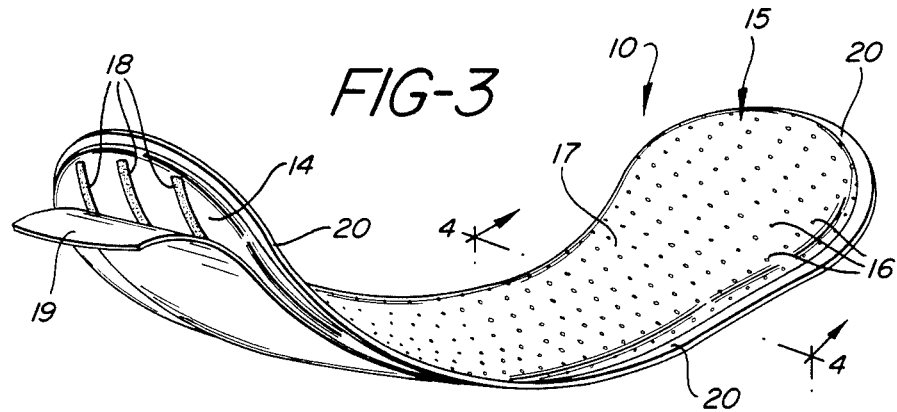
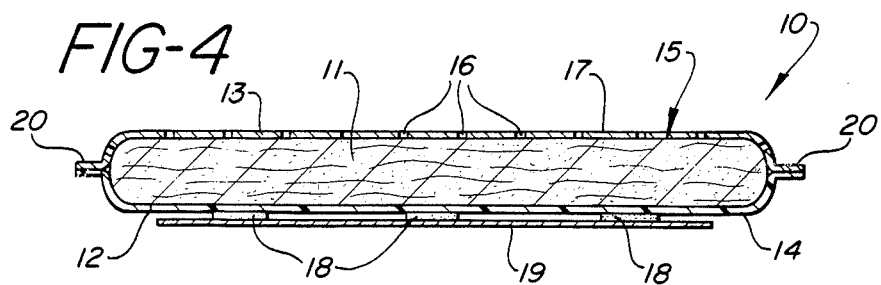

APERTURED FILM FACING AND METHOD OF MAKING THE SAME

BACKGROUND OF THE INVENTION

The present invention relates to absorbent products which typically contain an absorbent core overlaid or overwrapped with a facing or cover layer.

Apertured plastic films have been used to form the covers or facing layer of absorbent articles such as disposable diapers, sanitary napkins, and dressings. The films, being hydrophobic, are not wetted with body exudates and therefore, provided the exudate passes through the apertures of the film facing, the facing will remain clean, or non-staining, and dry. One difficulty encountered in using apertured films as covers or facings on absorbent products is that body exudates do not readily flow through the apertures of the film facing into the absorbent media. Various approaches have been taken to overcome this difficulty. In one approach absorbent material such as tissue is placed in close or touching contact with the under surface of the apertured film facing to "pull" the exudate through the film. However, the use of a tissue backing can contribute to strike back, or reverse flow, from the absorbent core to the face of the cover. In addition, as tissue may be stained with body exudate, the use of tissue backing may result in the stained tissue being visible through the apertures, and staining of the aperture edge.

In the apertured film facing of the present invention the edge of the apertures is coated with a hydrophilic material to promote fluid transfer through the apertures into the absorbent core of the absorbent article. Thus the apertured film facing of the present invention provides a clean dry facing with improved liquid transfer, avoiding the disadvantages of the prior art solutions by obviating the need for a tissue backing.

Other approaches taken to enhance the fluid transfer of apertured film facings involve the careful specification of aperture size and percentage open area of the film. U.S. Pat. No. 2,992,644 discloses an absorbent dressing with an apertured film facing with a preferred apertured size of from 0.01 to 0.2 inches in equivalent hydraulic diameter and an open area of from 10 to 40%, with a preferred thickness of less than one mil. U.S. Pat. No. 4,324,246 describes an absorbent articles with an apertured film facing having an open area of equal to or greater than 35%, and wherein at least 75% of the apertures have an equivalent hydraulic diameter equal to or greater than 0.025 inches, and having a thickness of less than 0.030 inches.

There are many processes for aperturing plastic film. U.S. Pat. Nos. 3,355,974, 3,719,736, 3,682,028, 3,526,349, 3,707,102 and 4,278,871 disclose processes for pin perforating plastic films. In the processes described therein, the aperture is not die cut, but is formed as the pin pierces the film, leaving a flap or flashing around the opening.

In the method of the present invention pins are used to aperture the film, and to apply a hydrophilic material to the edge of the apertures. U.S. Pat. No. 1,978,620 describes a method wherein, fibrous webs are pierced with needles, the needles dipped into a binder material, and removed from the web depositing the binder material on the web so as to bond the fibers around the formed hole.

Copending application Ser. No. 840,290, filed 3/14/86, describes an absorbent product with an apertured plastic film facing made from a bi-layer film. In the aperturing process the edge of the aperture becomes formed of the plastic composition of the top, or uppermost layer.

SUMMARY OF THE INVENTION

The present invention comprises an apertured plastic film facing material for an improved absorbent product, and the method of making the same, wherein the edge of the apertures is coated with hydrophilic material to promote fluid transfer through the facing to the absorbent core of the absorbent product. The present invention encompasses the use of any soft, supple hydrophobic plastic film. The apertures formed therein preferably have an equivalent hydraulic diameter of at least 0.025 inches. The distance between apertures is equal to or greater than 20% of the equivalent hydraulic diameter.

With the facing of the present invention, fluid transfer need not be regulated strictly by the size and/or configuration of the apertures, as the fluid transfer therethrough is enhanced by the coating of hydrophilic material. In addition, as mentioned above, a tissue backing or other means to draw fluid through the apertures is not needed, allowing greater latitude in the construction of an absorbent product utilizing the facing of the present invention. Lastly, the facing material of the present invention provides an absorbent product with a cleaner, dryer surface due to the hydrophilic coating of the apertures. In addition, the facing of the present invention provides a more opaque cover for an absorbent product in that smaller aperture sizes can be used while achieving fluid flow of larger apertures, by the use of the hydrophilic coating of the apertures, so that less of the underlying stain in the absorbent core is visible through the cover.

According to the method of the present invention a supply of film is brought into pressure contact with a the plurality of pins, or needles which are caused to extend through the film, and are then withdrawn for the film leaving the apertures. To apply the hydrophilic material to the edges of the apertures, the hydrophilic material may be coated on the pins prior to contacting the film with the pins, or the pins may be coated with hydrophilic material as they extend through the film, the coating being applied as the pins are withdrawn from the film.

In an alternate embodiment utilizing hollow needles, the hydrophilic material may be supplied through a hollow in the needle to a port at the tip of the needle, to coat the edge of the aperture as the needles pierce the film and/or when they are removed therefrom.

In another preferred embodiment, the pins or needles are heated to facilitate aperturing of the film and to permit the use of molten hydrophilic material. In a still preferred embodiment the pins or needles are heated to a temperature above the softening point but below the melting point of the film so as to avoid shrink back of the film from the pins or needles. Indeed, when the hydrophilic material is to be deposited in the apertures as the pins are removed from the film, it is essential that the temperature of the pins or needles be maintained below the melt point of the film.

BRIEF DESCRIPTION OF THE DRAWINGS

FIG. 1 is a schematic representation of a method for practicing the present invention.

FIG. 2 is an enlarged side view, in partial cross section, of a hollow needle which may be used to practice the method of the present invention.

FIG. 3 is a perspective view of an improved absorbent product in accordance with the present invention.

FIG. 4 is a cross-sectional view of the sanitary napkin of FIG. 3.

DETAILED DESCRIPTION OF THE INVENTION

Figure 5:
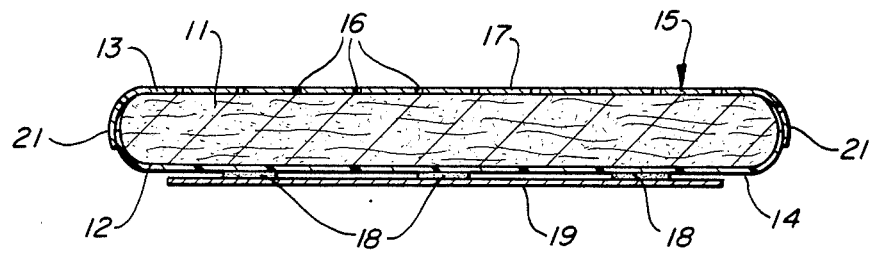
FIGS. 5 and 6 are cross-sectional views of sanitary napkins constructed using alternate techniques in accordance with the present invention.

The present invention comprises an apertured film facing material, and a method for making the same, wherein the apertures are coated with a hydrophilic material, and an improved absorbent product utilizing said facing. The hydrophilic material used to coat the edge of the apertures may be any known hydrophilic material suitable for use on an absorbent product, for example, hot water soluble polyvinyl alcohol, glycerine, guar gum, or hydroxyethylcellulose. The film used to make the facing of the present invention is a thin hydrophobic plastic film and may be, for example, a polyolefin, a vinyl, or an acrylic film. In a preferred embodiment the plastic of the film be compounded with titanium dioxide so as to enhance the opacity of the film. Opacity of the facing is desirable to "hide" the underlying absorbent core, especially once stained. In another preferred embodiment, the film should have a thickness in the range of 0.5 to 1.5 mils. If the film is too thin it will have insufficient strength when perforated to be used as a facing for an absorbent product. If the film is too thick it will be too stiff and non-conformable to be used as a facing for an absorbent product. In the most preferred embodiment, the apertured facing of the present invention is made from a one mil low density polyethylene film.

The apertures of the facing of the present invention preferably have an equivalent hydraulic diameter of at least 0.025 inches. The apertures may be larger, and may vary in size, and configuration. At equivalent hydraulic diameters of 0.05 inches or more, apertured plastic film facings exhibit strike back or reverse flow of the fluid from the absorbent core to the outer surface of the facing. As the hole size is reduced, fluid strike back is reduced. In the invention of the present application wherein the apertures are coated with hydrophilic material, to promote fluid flow through the apertures, rapid fluid transfer through the facing material can be achieved at smaller hole sizes than with uncoated apertures.

The percentage open area of the facing should be sufficient to allow complete transfer of the fluid through the facing so as to leave a clean dry surface on the facing. Generally, open areas of greater than 35% are used. As thin films are used to form the apertured facing of the present invention, too great an open area can reduce the strength of the film to the point where it is no longer acceptable as a facing material. In general the distance between apertures should be equal to or greater than 20% of the equivalent hydraulic diameter of the apertures to maintain adequate strength in the facing material. Good results have been achieved in the facing of the present invention with 150 holes per square inch on 0.056 inch centers yielding a 37% open area. Good results were also achieved with the facing of the present invention having 195 holes per square inch on 0.048 inch centers, yielding a 35% open area.

The method of the present invention will be described in relation to FIG. 1. According to the method of the present invention, a hydrophobic plastic film sheet 1 is supplied and placed in pressure contact with pins 3. The pins are provided on a rotatable roll 4 so as to provide a continuous process. In the apparatus depicted in FIG. 1 the pressure contact is achieved through the use of guide rolls 2 and 6 which are not in alignment with (e.g. the surfaces of which do not fall in a straight line with) the surface of the pins. The pressure contact of the pins with the film, caused by the offset of the pins and the carrier rolls, causes the pins to puncture the film and extend therethrough forming apertures in the film. As shown in FIG. 1 a hydrophilic agent may be applied to the ends of the pins by e.g., dipping the ends of the pins into a bath 5 of hydrophilic solution while the pins extend through the film. As the film moves away towards carrier roll 6, the pins are withdrawn from the film and the edges of the apertures are coated with a hydrophilic material.

In another embodiment of the method of the present invention, the hydrophilic agent may be applied to the pins prior to placing the pins in pressure contact with the film. In this embodiment the edges of the apertures are coated with hydrophilic material as the pins puncture the film. In this embodiment or the embodiment depicted in FIG. 1, the hydrophilic material may be applied to the pins by kiss coating the pins with a brush, sponge, or fabric to which hydrophilic material has been added.

In an alternative embodiment, the pins may be provided along a flat surface which is raised and lowered along a line tangential to the film, to bring the pins into pressure contact with the film, and cause the pins to puncture the film and extend therethrough, forming apertures in the film.

In another alternative embodiment the pins may comprise hollow needles such as the hollow needle as shown in FIG. 2. The hollow needle 7 has channel 8 for delivering the hydrophilic material to the tip of the needle, through the port 9 located at the tip of the needle.

In perforating the plastic film, the pins or needles may be heated so as to make a smoother aperture in the film. When heating the pins or needles it is preferred to maintain the temperature thereof above the softening point but below the melt point of the film. If the temperature is above the melt point of the film, the film will shrink back from the pin, which may cause an uneven surface or surface roughness which is unacceptable in a facing material. In addition, in those embodiments of the method of the present invention where the hydrophilic material was applied to the pins as the pins pierce and extend through the film, it is necessary to keep the temperature of the pins below the melt point of the film because if the film shrinks away from the pins, it is difficult to reverse coat the edge of the apertures as the pins are withdrawn from the film. With certain films and particularly with very thin films, it may be necessary to carry the film through the process on a release paper in order to facilitate removal from the pins. The preferred embodiment of the method of the present invention utilizes a 1 mil, low density polyethylene film and a pin temperature of 110° C.

The apertured film facing material of the present invention may be used to form an improved absorbent product such as that shown at 10 in FIGS. 3 to 6. The absorbent product comprises an absorbent core 11 having first and second opposed faces, 12 and 13 respectively. A liquid impermeable back sheet 14 overlies the first opposed face of the absorbent core and a liquid permeable top sheet 15 overlies the second opposed face of the absorbent core. The liquid permeable top sheet comprises a hydrophobic film having a multiplicity of apertures 16 therein, the edge of the apertures being coated with hydrophilic material to promote fluid transfer through the apertures into the absorbent core.

The use of the facing of the present invention provides an improved absorbent product with a cleaner, drier appearance and feel. The coating of the apertures with hydrophilic material promotes fluid transfer through the facing into the absorbent core, leaving the surface 17 cleaner and drier. In addition, by coating the apertures to provide better fluid transfer therethrough, smaller apertures may be used to achieve the fluid transfer of larger uncoated apertures, while providing better opacity or cover of the underlying absorbent core, especially when stained. Further the coating of the edge of the apertures allows the use of apertures of varying configuration, such as a diamond shape, which may be formed by pins or needles of a diamond shaped cross-section.

The absorbent core 11 is sealed between the liquid impermeable backsheet 14 and the liquid permeable top sheet 15 in a manner described hereinbelow. The absorbent core 11 may be comprised of any of the well known absorbents such as wood pulp, rayon, synethtic absorbents in the form of fibers, powder, or foam or combinations thereof. Absorbency enhancers such as the so called "superabsorbent" materials may be employed. Non-hydrophilic materials may also be employed in combination with absorbent materials. One such example is a low density, thermal bonded nonwoven fabric comprising a mixture of absorbent fibers and staple length polyester/polyethlene conjugate thermoplastic fibers. The absorbent fibers may be wood pulp or other cellulosic fibers which may have been treated to enhance absorbency. Suitable conjugate fibers are fibers which comprise a polyester core surrounded by a sheath of polyethylene. A highly satisfactory absorbent core is produced by a thermally bonded absorbent fabric comprising 54% by weight of wood pulp fibers and 46% by weight of conjugate fibers having a staple length of 3.81 centimeters and a denier of 3.0. The fabric is stabilized by passing hot air through the fibers and thereby melting the polyethylene which bonds the fibers together upon cooling. Such a fabric is capable of holding about seventeen times its own weight of distilled water. Alternatively, an absorbent batt of densified web material may be employed, as described in U.S. Pat. No. 4,551,142.

The fluid impermeable backsheet 14 acts as a barrier to body fluids and prevents staining of the undergarments of the user. The backsheet may comprise any thin, flexible body fluid impermeable material such as a polymeric film, e.g., polyethylene,polypropylene, or cellophane. Alternatively the barrier may comprise a normally fluid pervious material that has been treated to be impervious such as impregnated fluid repellant paper. If desired, the backsheet 14 may be adhesively affixed to the garment facing side of the absorbent batt 11.

Disposed on the garment facing side of the backsheet 14 are longitudinally extending pressure sensitive adhesive means 18 provided for attaching the napkin to the crotch portion of an undergarment. While such adhesive means are illustrated in the form of longitudinally extending lines, it will be understood that various patterns such as spots or transverse lines are suitable. The adhesive employed may be any of the large number of pressure sensitive adhesives that are commercially available, including water based adhesives such as acrylate adhesives, e.g., vinyl acetate/2-ethyl-hexyl acrylate copolymer which may be combined with tackifiers. Alternatively the adhesive may also comprise a pressure sensitive rapid setting hot melt adhesive. The adhesive element may also comprise a double faced tape.

Overlying the adhesive means 18 is a protective release strip 19 which is provided to protect the adhesive means from dirt and unintended adhesion prior to use. The release strip 19 may be constructed of any suitable sheet-like material which adheres with sufficient tenacity to the adhesive means to remain in place prior to use but which can be readily removed when the napkin is to be used. A particularly useful material is a semibleached kraft paper, the adhesive contacting side of which has been silicone treated to provide easy release from the adhesive means 18.

Figure 6:
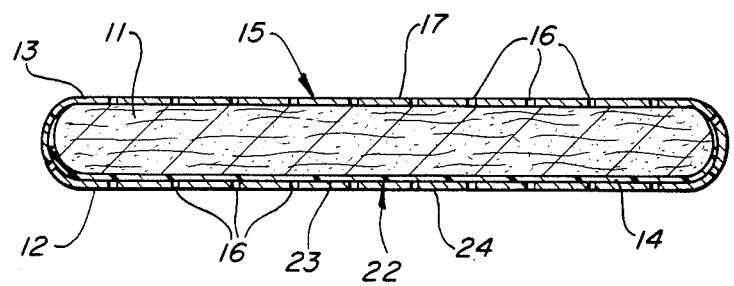

As seen in FIGS. 3 and 4 the liquid permeable top sheet 15 may be thermally bonded to the backsheet 14 about the periphery 20 of the absorbent product 10. In FIGS. 3 and 4 the bonded periphery 20 is seen to be outwardly extending from the absorbent product. Alternatively the backsheet 14 may be folded upward around the edges of the absorbent core 11, and the top sheet 15 folded over the back sheet edges and thermally bonded at the overlap 21 as shown in FIG. 5. This technique gives the edges of the napkin a more rounded and comfortable appearance. In other absorbent product applications it may be desirable to completely enclose the absorbent core 11 in an apertured film cover as shown in FIG. 6. In this embodiment the top sheet 15 surrounds the absorbent core 11 and the back sheet 14, with the edges of the top sheet adjoining each other at a seam indicated at 22. On either side of the seam the cover formed by the top sheet is thermally bonded to the underlying back sheet 14, as indicated at 23 and 24. At the longitudinal ends of the napkin the product may be sealed by thermal bonding the edge of the body facing side of the cover to the edge of the garment facing side of the cover.

What is claimed is:

1. An apertured film facing material comprising a thin flexible hydrophobic plastic film having apertures therein, the edge of said apertures being coated with a hydrophilic material to promote fluid transfer through the apertures.

2. The apertured film facing material of claim 1 wherein the distance between the apertures is greater than about 20% of the diameter of the apertures.

3. An apertured film facing material as in claim 2 wherein said apertures have an equivalent hydraulic diameter of 0.025" inches or more.

4. An apertured film facing material as in claim 1 wherein said hydrophilic material is polyvinyl alcohol, glycerine, grain, gum, or hydroxyethyl cellulose.

5. The apertured film facing material of claim 1 wherein said film has a thickness of 0.5 to 1.5 mils.

6. The apertured film facing material of claim 1 wherein said film is 1 mil low density polyethylene film.

* * * * *